(12) United States Patent
Nagashima (10) Patent No.: US 10,238,275 B2
(45) Date of Patent: Mar. 26, 2019

(54) LIGHT SOURCE DRIVING APPARATUS, LIGHT SOURCE DRIVING METHOD, AND LIGHT SOURCE APPARATUS

(71) Applicant: SONY CORPORATION, Tokyo (JP)

(72) Inventor: Zenya Nagashima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/560,180

(22) PCT Filed: Mar. 7, 2016

(86) PCT No.: PCT/JP2016/001216
§ 371 (c)(1),
(2) Date: Sep. 21, 2017

(87) PCT Pub. No.: WO2016/157732
PCT Pub. Date: Oct. 6, 2016

(65) Prior Publication Data
US 2018/0092522 A1 Apr. 5, 2018

(30) Foreign Application Priority Data
Mar. 31, 2015 (JP) ................................ 2015-071748

(51) Int. Cl.
*A61B 1/06* (2006.01)
*A61B 1/00* (2006.01)
(Continued)

(52) U.S. Cl.
CPC .............. *A61B 1/0661* (2013.01); *A61B 1/00* (2013.01); *A61B 1/00004* (2013.01);
(Continued)

(58) Field of Classification Search
None
See application file for complete search history.

(56) References Cited

U.S. PATENT DOCUMENTS 6,259,466 B1* 7/2001 Oomura .................. B41J 2/471
347/237
2009/0180786 A1* 7/2009 Arahira .............. H04B 10/5165
398/189
(Continued)

FOREIGN PATENT DOCUMENTS

JP 2006-000157 A 1/2006
JP 2013-111176 A 6/2013

OTHER PUBLICATIONS

International Search Report and Written Opinion of PCT Application No. PCT/JP2016/001216, dated May 24, 2016, 06 pages of ISRWO.

*Primary Examiner* — Jany Richardson
(74) *Attorney, Agent, or Firm* — Chip Law Group (57) ABSTRACT

A light source driving apparatus according to an embodiment of the present technology includes a reception unit, an output unit, a sample unit, and a timing output unit. The reception unit receives a pulse modulation signal for pulse-driving a light source. The output unit outputs a delay modulation signal obtained by delaying the received pulse modulation signal to the light source. The sample unit samples, at a predetermined timing, a light amount of the light source driven on the basis of the delay modulation signal. The timing output unit outputs, to the sample unit, a pulse fall timing of the received pulse modulation signal as the predetermined timing.

8 Claims, 4 Drawing Sheets

(51) Int. Cl.
*G02B 23/26* (2006.01)
*G02B 23/24* (2006.01)

(52) U.S. Cl.
CPC ............ *A61B 1/00133* (2013.01); *A61B 1/06* (2013.01); *G02B 23/2469* (2013.01); *G02B 23/26* (2013.01)

(56) References Cited

U.S. PATENT DOCUMENTS

| | | | | |
|---|---|---|---|---|
| 2009/0256973 | A1* | 10/2009 | Bazzani | G09G 3/3426 348/744 |
| 2014/0042924 | A1* | 2/2014 | Lee | H05B 37/02 315/210 |
| 2017/0319055 | A1* | 11/2017 | Innami | A61B 1/07 |

* cited by examiner

LIGHT SOURCE DRIVING APPARATUS, LIGHT SOURCE DRIVING METHOD, AND LIGHT SOURCE APPARATUS

CROSS REFERENCE TO RELATED APPLICATIONS

This application is a U.S. National Phase of International Patent Application No. PCT/JP2016/001216 filed on Mar. 7, 2016, which claims priority benefit of Japanese Patent Application No. JP 2015-071748 filed in the Japan Patent Office on Mar. 31, 2015. Each of the above-referenced applications is hereby incorporated herein by reference in its entirety.

TECHNICAL FIELD

The present technology relates to a light source apparatus, a light source driving apparatus that drives this, and a light source driving method.

BACKGROUND ART

Patent Literature 1 discloses an endoscope system that includes two observation modes. In a first normal observation mode, a normal observation image of a paries illuminated by white light is displayed on a display apparatus. In a second special observation mode, a synthetic image obtained by synthesizing an image obtained by illuminating white light with an image of fluorescence generated from a lesion location due to excitation is displayed. For generating the synthetic image, white light and excitation light are alternately irradiated onto the paries via a light guide of the endoscope system (paragraphs [0003], [0004], etc. in specification).

As shown in FIG. 3 of Patent Literature 1, in a light source part of the endoscope system, a dichroic mirror transmits white light and also reflects laser light output as excitation light from a semiconductor laser is provided. An amount of laser light left unreflected by the dichroic mirror is detected by a photodiode and output to an APC (Automatic Power Control) circuit. With this configuration, it becomes possible to instantaneously and highly precisely feedback-control the optical output amount of the semiconductor laser (paragraphs [0040], [0043], [0044], etc. in specification).

CITATION LIST

Patent Literature

Patent Literature 1: Japanese Patent Application Laid-open No. 2006-157

DISCLOSURE OF INVENTION

Technical Problem

For executing APC, there is a need to sample a light amount of a light source. A technology that enables sampling to be performed at appropriate timings without raising loads of a processor and the like equipped in a light source apparatus in a case where the light source for white light and the light source for excitation light are driven alternately as described in Patent Literature 1, a case where each of the light sources are pulse-driven, and the like, is being demanded.

In view of the circumstances as described above, the present technology aims at providing a light source driving apparatus that enables sampling to be performed at appropriate timings without raising loads of a processor and the like, a light source driving method, and a light source apparatus that uses this.

Solution to Problem

For attaining the object described above, a light source driving apparatus according to an embodiment of the present technology includes a reception unit, an output unit, a sample unit, and a timing output unit.

The reception unit receives a pulse modulation signal for pulse-driving a light source.

The output unit outputs a delay modulation signal obtained by delaying the received pulse modulation signal to the light source.

The sample unit samples, at a predetermined timing, a light amount of the light source driven on the basis of the delay modulation signal.

The timing output unit outputs, to the sample unit, a pulse fall timing of the received pulse modulation signal as the predetermined timing.

In this light source driving apparatus, the delay modulation signal obtained by delaying the received pulse modulation signal is output to the light source. Then, the pulse fall timing of the received pulse modulation signal is output to the sample unit so that the light amount of the light source is sampled at that timing. As a result, it becomes possible to perform sampling at appropriate timings without raising loads of a processor and the like.

The reception unit may receive a stationary signal for stationarily driving the light source. In this case, the light source driving apparatus may further include a judgment unit that judges which of the pulse modulation signal and the stationary signal a signal received by the reception unit is. Further, the timing output unit may output, in a case where a result of the judgment by the judgment unit is the stationary signal, a stationary drive timing for sampling a light amount of the light source to be stationarily driven.

Accordingly, appropriate sampling becomes possible even in a case where the light source is stationarily driven.

The stationary drive timing may be a preset fixed timing.

Accordingly, it becomes possible to easily perform sampling while suppressing loads.

The reception unit may be capable of receiving the pulse modulation signal or the stationary signal output from an external apparatus.

For example, in a case where a light source is driven so as to be synchronized with operations of the external apparatus, and the like, a pulse modulation signal or the like may be output from the external apparatus. In such a case, by using the present technology, sampling can be executed at appropriate timings without raising loads of the processor and the like on the light source side.

The sample unit may store a sampling result after an elapse of a predetermined response time since the predetermined timing. In this case, the output unit may cause the pulse modulation signal to be delayed by a time longer than the predetermined response time.

Accordingly, an appropriate sampling result can be obtained.

A light source driving method according to an embodiment of the present technology includes outputting a delay modulation signal obtained by delaying a pulse modulation signal for pulse-driving a light source, to the light source.

A light amount of the light source driven on the basis of the delay modulation signal is sampled at a pulse fall timing of the received pulse modulation signal.

A light source apparatus according to an embodiment of the present technology includes a light source, the reception unit, the output unit, the sample unit, the timing output unit, and a control unit.

The control unit controls an output of the light source on the basis of a result of the sampling by the sample unit.

In this light source apparatus, it becomes possible to perform sampling at appropriate timings without raising a load of the control unit and highly accurately control the output of the light source.

Advantageous Effects of Invention

As described above, according to the present technology, it becomes possible to perform sampling at appropriate timings without raising loads of the processor and the like. It should be noted that the effects described herein are not necessarily limited, and any effect described in the present disclosure may be obtained.

MODE FOR CARRYING OUT THE INVENTION

Hereinafter, an embodiment of the present technology will be described with reference to the drawings.

(Endoscope Apparatus)

Figure 1:
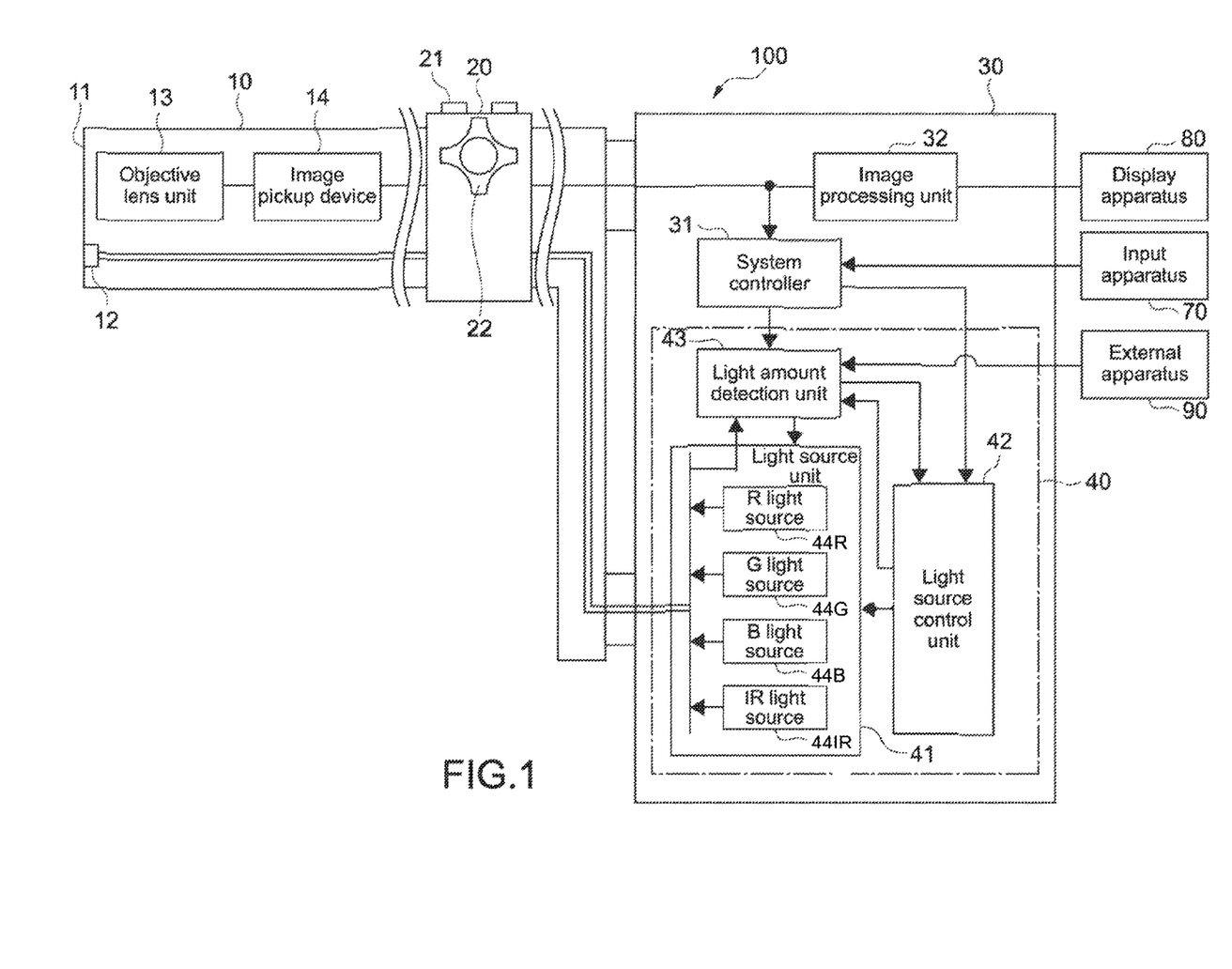
FIG. 1 A block diagram showing a configuration example of an endoscope apparatus according to an embodiment.

FIG. 1 is a block diagram showing a configuration example of an endoscope apparatus according to an embodiment of the present technology. An endoscope apparatus 100 includes an insertion unit 10, an operation unit 20, and a body unit 30.

The insertion unit 10 is a flexible part to be inserted into a paries. At a tip end portion 11 of the insertion unit 10, an irradiation port 12 for illumination light to be irradiated onto a to-be-observed area is provided. Also provided at the tip end portion 11 are an objective lens unit 13 and an image pickup device 14 for acquiring image information of the to-be-observed area. As the image pickup device 14, for example, a CMOS (Complementary Metal Oxide Semiconductor) sensor, a CCD (Charge Coupled Device) sensor, or the like is used.

The operation unit 20 is connected to a base end of the insertion unit 10. Various switches 21, an angle knob 22, and the like are provided in the operation unit 20. For example, by operating the switch 21, air, water, or the like is supplied to the to-be-observed area via a supply port (not shown). Further, by operating the angle knob 22, a curvature mechanism provided at the tip end portion 11 is operated so that the tip end portion 11 is curved in an arbitrary direction at an arbitrary angle. A forceps port into which a treatment tool such as forceps and electrodes is inserted, and the like may be provided in the operation unit 20.

The body unit 30 includes a system controller 31, an image processing unit 32, and a light source apparatus 40 according to the present technology. The system controller 31 collectively controls the entire system of the endoscope apparatus 100. For example, the system controller 31 instructs the light source apparatus 40 to emit predetermined illumination light and, in synchronization with this, causes the image pickup device 14 to acquire image information of a to-be-observed area.

Further, as shown in FIG. 1, an input apparatus 70 is connected to the system controller 31 via an input/output interface (not shown). The input apparatus 70 is, for example, a device that is operated by an operator, such as a keyboard, a mouse, and a touch panel. The system controller 31 executes processing corresponding to an operation input via the input apparatus 70.

The system controller 31 includes, for example, a CPU, a RAM, a ROM, and the like and controls the entire system by the CPU loading a control program recorded in advance in the ROM in the RAM and executing it. The configuration of the system controller 31 is not limited, and arbitrary hardware and software may be used. For example, devices such as FPGA (Field Programmable Gate Array) and ASIC (Application Specific Integrated Circuit) may be used.

The image processing unit 32 executes various types of image processing such as color interpolation and gamma correction on image information output from the image pickup device 14. The image information processed by the image processing unit 32 is output to a display apparatus 80 connected to the body unit 30. The display apparatus 80 is a display device that uses, for example, liquid crystal, EL (Electro-Luminescence), or the like.

(Light Source Apparatus)

The light source apparatus 40 includes a light source unit 41, a light source control unit 42, and a light amount detection unit 43. The light source unit 41 includes a plurality of laser light sources (LDs) 44. In this embodiment, a red laser light source 43R, a green laser light source 43G, a blue laser light source 43B, and an infrared laser light source 43IR are provided. Laser light emitted from each of the laser light sources 43 enters a light guide (optical fiber) 44 connected to the light source unit 41 via an optical system (not shown) and is then guided to the illumination port 12 provided at the tip end portion 11 of the insertion unit 10 via the light guide 45.

The red laser light source 44R, the green laser light source 44G, and the blue laser light source 44B are driven when irradiating white light onto the to-be-observed area, for example. For example, white light is generated by synthesizing respective laser light of RGB by an optical system (not shown) in the light source unit 41. Alternatively, the to-be-observed area may be irradiated while the respective laser light of RGB are switched at high speed. The infrared laser light source 44IR is used as a light source for excitation light for exciting a fluorescent pigment injected into a human body, for example. Hereinafter, white light may be referred to as normal light, and excitation light excluding light of the respective colors of RGB and the like may be referred to as special light.

The number and types of laser light sources 44 (wavelength range of emission light, etc.) to be arranged in the light source unit 41 are not limited. Further, other solid-state light sources such as an LED, a xenon lamp, and the like may also be arranged in the light source unit 41.

The light source control unit 42 controls start and stop of an operation of each of the laser light sources 44 and also controls a current amount to be input to each of the laser light sources 44. In other words, the light source control unit 42 is capable of controlling an output (optical output) of each of the laser light sources 44. For example, a microprocessor in which a CPU, a memory (RAM, ROM), I/O (Input/Output), and the like are mounted on 1 chip, or the like is used as the light source control unit 42. The FPGA, ASIC, or the like described above may also be used.

The light amount detection unit 43 samples a light amount of laser light emitted from each of the laser light sources 44 and feeds back the sampling result to the light source control unit 42. For example, in a case where each of the laser light sources 44 performs pulse drive on the basis of pulse modulation signals, there is a need to perform sampling at a timing where the laser light sources 44 are lit. The pulse drive as described above is executed in a case of PWM (Pulse Width Modulation)-controlling each of the laser light sources 44, a case of alternately irradiating normal light and special light at high speed, and the like.

In a case where the light source control unit 42 generates pulse modulation signals and outputs them to the light source unit 41, the light source control unit 42 can generate appropriate sampling timings on the basis of the pulse modulation signals generated by itself. In other words, it is possible to generate sample signals (pulse signals) by itself on the basis of the pulse modulation signals and output them to a sample hold circuit (hereinafter, referred to as S/H circuit).

On the other hand, as shown in FIG. 1, pulse modulation signals may be output to the light source unit 41 from an external apparatus 90 connected to the body unit 30. For example, it is assumed that an image of normal light and image of special light are photographed alternately by an external image pickup apparatus. In this case, for driving the laser light sources 44 in synchronization with a photographing operation of the external image pickup apparatus, pulse modulation signals are output from the external apparatus.

In a case where the pulse modulation signals are output from the external apparatus, it is difficult to detect an appropriate sampling timing. For example, the pulse modulation signals from the external apparatus are caused to be once input to the light source control unit 42 so that the light source control unit 42 outputs pulse modulation signals while referencing those signals. Accordingly, while it becomes possible to detect appropriate sample timings, there is a fear of an adverse influence such as unnecessary loads being placed on the microprocessor and the like configuring the light source control unit 42.

The light amount detection unit 43 according to the present technology is capable of receiving pulse modulation signals and executing sampling at appropriate timings on the basis of the received pulse modulation signals. Accordingly, even in a case where pulse modulation signals are output from an external apparatus, sampling can be executed at appropriate timings without raising a load of the light source control unit 42.

Further, also in a case where the pulse modulation signals are output from the light source control unit 42, appropriate sampling can be executed on the basis of the pulse modulation signals. Furthermore, for synchronizing the photographing operation by the image pickup device 14 of the endoscope apparatus 100 and the drive of the laser light sources 44, the pulse modulation signals may be output from the system controller 31. Even in such a case, appropriate sampling can be executed by the light amount detection unit 43, and thus the load on the light source control unit 42 can be suppressed.

(Light Amount Detection Unit)

Figure 2:
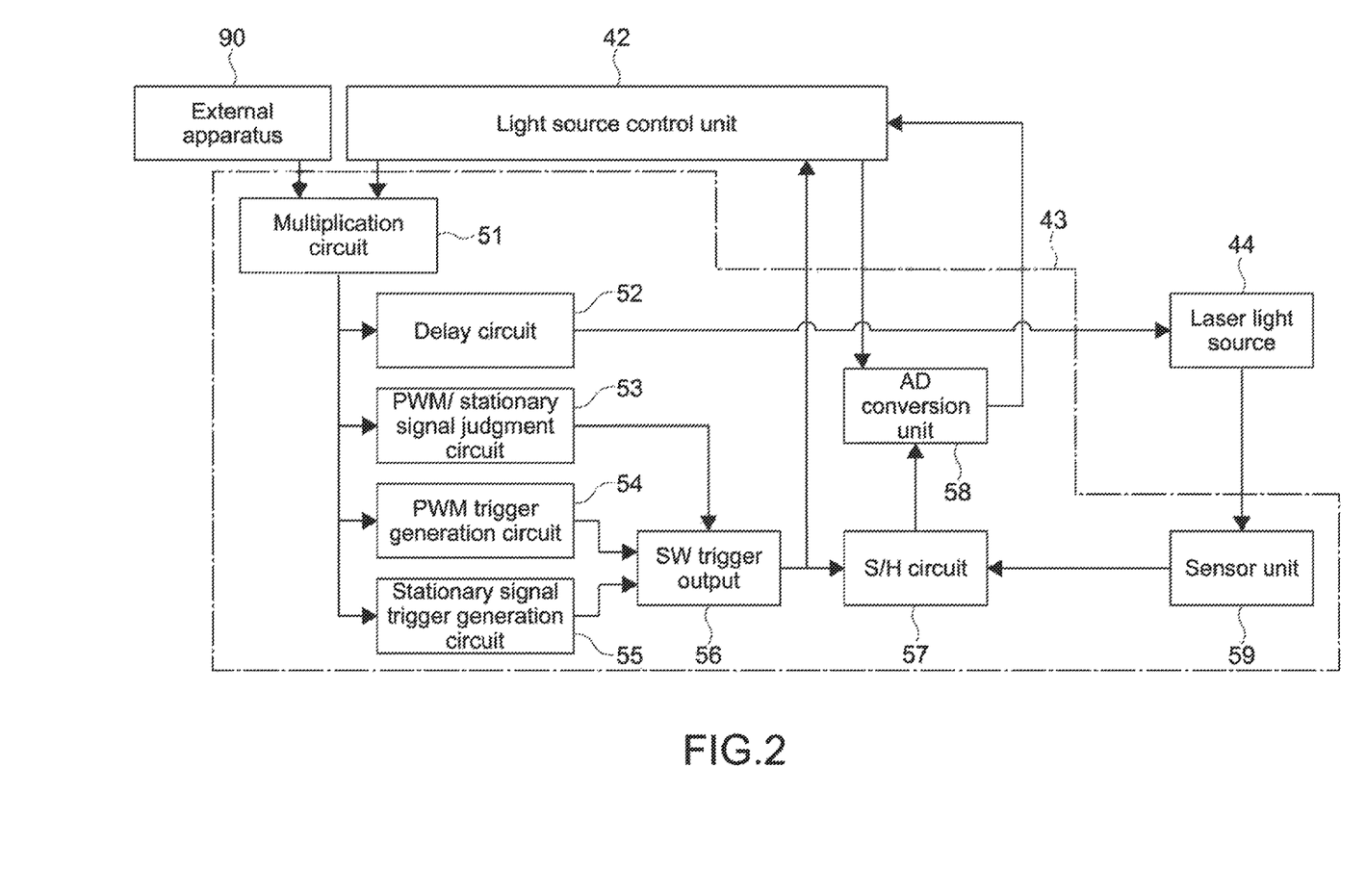
FIG. 2 A block diagram showing a configuration example of a light amount detection unit shown in FIG. 1.

The light amount detection unit 43 will be described while taking a case of PWM-controlling each of the laser light sources 44 as an example. FIG. 2 is a block diagram showing a configuration example of the light amount detection unit 43.

The light amount detection unit 43 includes a multiplication circuit 51, a delay circuit 52, a signal judgment circuit 53, a PWM trigger generation circuit 54, a stationary signal trigger generation circuit 55, an output switch 56, an S/H circuit 57, an AD conversion unit 58, and a sensor unit 59.

The multiplication circuit 51 receives a pulse modulation signal and a stationary signal output from the light source control unit 42 or the external apparatus 90 (may also be system controller 31). Typically, a signal from either one of the light source control unit 42 and the external apparatus 90 is received on the basis of a setting made by an operator and the like. The present technology is not limited to this, and even in a case where two or more pulse modulation signals output from both of them are received, those signals can be processed collectively by multiplying those signals. It should be noted that the stationary signal is a signal for stationarily driving the laser light sources 44, that is, a signal for emitting continuous light.

The delay circuit 52 causes the received pulse modulation signal to be delayed and outputs it to the laser light sources 44. Hereinafter, the delayed pulse modulation signal will be referred to as delay modulation signal. In this embodiment, the laser light sources 44 are pulse-driven on the basis of delay modulation signals output from the delay circuit 52.

The signal judgment circuit 53 judges which of a PWM pulse modulation signal and a stationary signal for stationary drive the signal received by the multiplication circuit 51 is. The PWM trigger generation circuit 54 outputs a sample timing for sampling the light amount of the laser light sources 44 on the basis of the pulse modulation signal received by the multiplication circuit 51. Specifically, a trigger signal (S/H signal) that becomes a HI level at the sample timing is output.

The stationary signal trigger generation circuit 55 outputs a stationary drive timing for sampling the light amount of the laser light sources 44 to be stationarily driven. Also in this case, an S/H signal that becomes a HI level at the sample timing is output.

The output switch 56 causes, on the basis of the judgment result of the signal judgment circuit 53, either one of the PWM S/H signal and the S/H signal for the stationary signal to pass through and outputs it to the S/H circuit 57. In this embodiment, since a conversion operation of the AD conversion unit 58 is controlled by the light source control unit 42, the S/H signal is also output to the light source control unit 42 for a command transmission of the conversion operation.

The PWM trigger generation circuit 54, the stationary signal trigger generation circuit 55, and the output switch 56 realize a timing output unit according to this embodiment.

The sensor unit 59 detects the light amount of laser light output from the laser light sources 44. In this embodiment, a photodiode is used as the sensor unit 59, and signals corresponding to the received light amounts (hereinafter, referred to as PD signals) are output to a monitor. Although illustrations are omitted in FIG. 1, a predetermined optical system including a half mirror and the like is arranged on an optical path between the light source unit 41 and the light guide 45 so that the light from the light source unit 41 is guided to the photodiode, for example. It should be noted that TIA (TransImpedance Amplifier) and the like may also be used for the photoelectric conversion.

The PD signals output from the sensor unit 59 are amplified by, for example, an operational amplifier circuit or the like and output to the S/H circuit 57. If necessary, an offset may be removed by a subtraction circuit or the like.

The S/H circuit 57 samples the light amount of the laser light sources 44 driven on the basis of the delay modulation signals at a predetermined timing. In this embodiment, sampling is executed on the basis of the PWM S/H signal output from the output switch 56. Therefore, the sampling is executed at a timing where the S/H signal becomes a HI level.

The S/H circuit 57 also samples the light amount of the laser light sources 44 driven on the basis of the stationary signals at a predetermined timing. In this case, sampling is executed at a timing where the S/H signal for the stationary signal output from the output switch 56 becomes a HI level. In other words, in both the pulse drive and the stationary drive, the timing where the S/H signal becomes a HI level becomes the predetermined timing described above.

The sampling result held by the S/H circuit 57 is converted by the AD conversion unit 58 and fed back to the light source control unit 42. The light source control unit 42 executes APC on the basis of the sampling result. Accordingly, the light amount of the laser light sources 44 can be maintained constant.

Specific configurations of the respective blocks shown in FIG. 2 and the like are not limited, and arbitrary configurations may be used. For example, the respective blocks can be realized by using hardware such as a well-known delay circuit and judgment circuit, arbitrary software, and the like. The FPGA, ASIC, and the like described above may also be used.

Figure 3:
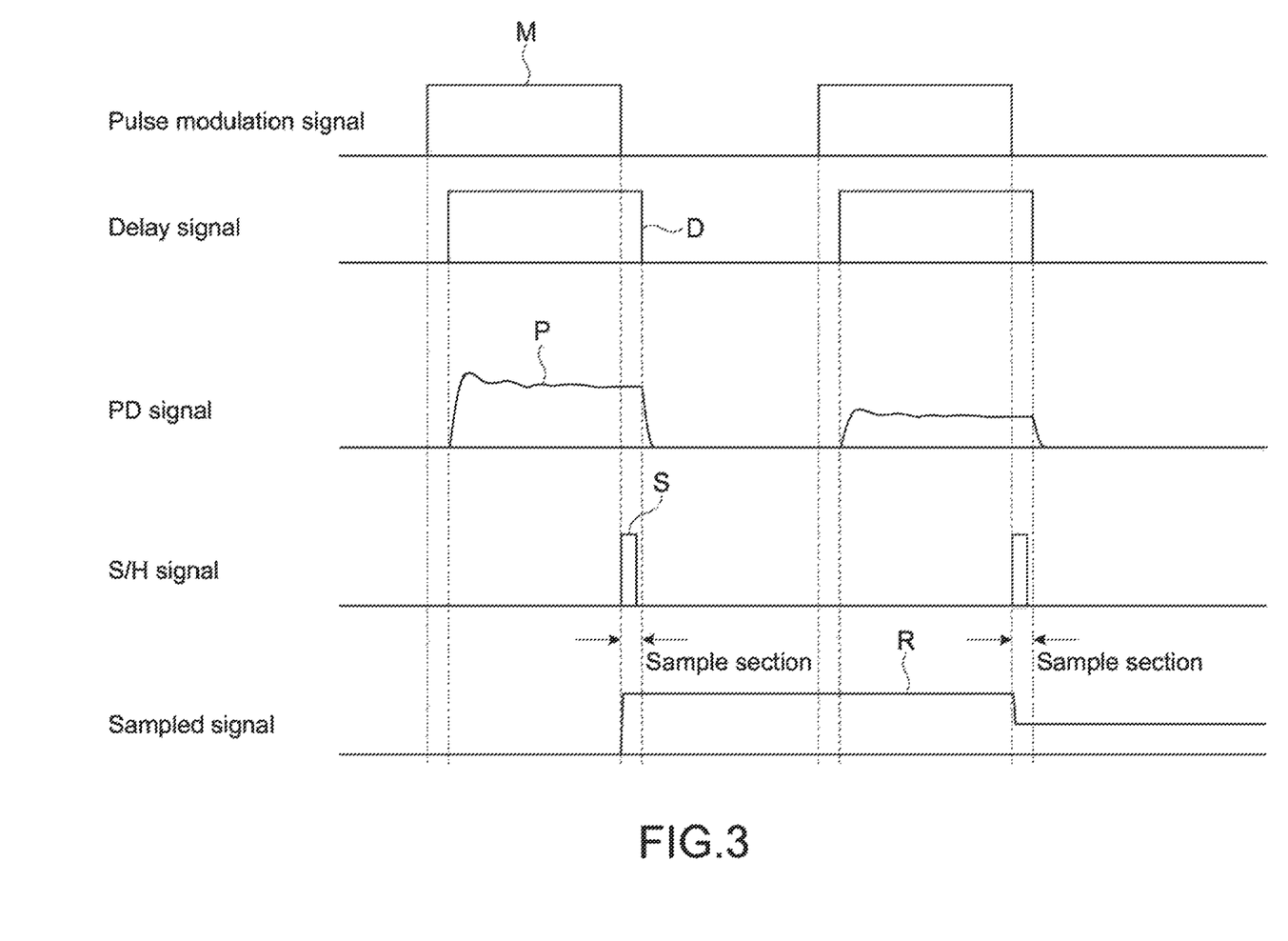
FIG. 3 A timing chart diagram showing an operation example for sampling a light amount of a laser light source.

FIG. 3 is a timing chart diagram showing an operation example for sampling the light amount of the laser light sources 44. As a pulse modulation signal M is input to the multiplication circuit 51, the delay circuit 52 generates and outputs a delay modulation signal D. At this time, it is also possible to control the operation of the delay circuit 52 in accordance with the judgment result obtained by the signal judgment circuit 53. On the other hand, delay processing may automatically be executed along with the reception of the pulse modulation signal M, irrespective of the judgment result.

It should be noted that the judgment by the signal judgment circuit 53 is executed by a rising or falling edge detection of the pulse modulation signal M, for example. It is judged as a pulse modulation signal in a case where an edge is detected and judged as a stationary signal in a case where an edge is not detected for a certain time or more. Other judgment methods may be executed instead.

The sensor unit 59 generates a PD signal P corresponding to the light amount of the laser light sources 44 driven on the basis of the delay modulation signal D and outputs it to the S/H circuit 57. On the basis of the judgment result obtained by the signal judgment circuit 53, a PWM S/H signal S is output from the output switch 56 to the S/H circuit 57.

As shown in FIG. 3, the PWM S/H signal S is generated such that the falling edge of the pulse modulation signal M input to the multiplication circuit 51 becomes a trigger timing. In other words, the falling timing of the pulse modulation signal M is output to the S/H circuit 57 as the sample timing.

Accordingly, the PD signal P right before the falling edge of the PD signal P, that is, right before a lighting period ends, is sampled. The sampled signal R is held until the next sampling. The light source control unit 42 can highly accurately execute APC on the basis of a change of the sampled signal R.

A delay length of the delay modulation signal D with respect to the pulse modulation signal M is set as appropriate on the basis of a response time of the S/H circuit 57. The S/H circuit 57 holds a result of the sampling after an elapse of a response time requisite for executing sampling. The delay circuit 52 causes the pulse modulation signal M to be delayed while using a time longer than this response time as the delay length.

Accordingly, with a section between the falling edge of the pulse modulation signal M and the falling edge of the PD signal P being a sample section, it becomes possible to perform appropriate sampling on the basis of the S/H signal S having a pulse width corresponding to the response time. In a case where the delay length is shorter than the response time, sampling is highly likely to be performed while also including a time during which the laser light sources 44 are unlit. It should be noted that the response time is a parameter that depends on characteristics of the S/H circuit 57.

In a case where a stationary signal is input to the multiplication circuit 51, the S/H signal for the stationary signal is output from the output switch 56 (omitted in timing chart) on the basis of the result of the signal judgment circuit 53. Accordingly, appropriate sampling can be performed even in a case where the laser light sources 44 are stationarily driven.

In the case of stationary drive, the laser light sources 44 constantly emit light, so intervals of the sampling timings, that is, S/H signal pulses may be arbitrary. Therefore, a fixed sample timing may be determined in advance and stored in a storage unit of the light source apparatus 40 or the like. Then, an S/H signal corresponding to that timing may be output by the stationary signal trigger generation circuit 55. Further, since an output of the S/H signal is selected as appropriate by the output switch 56, the stationary signal trigger generation circuit 55 may operate in free running independent from other blocks. Accordingly, the light amount of the laser light sources 44 to be stationarily driven can be sampled with ease.

It should be noted that regarding the sample timing for the stationary drive, since a time during which APC is not executed becomes longer as the interval of timings becomes longer, control accuracy of the output of the laser light sources 44 may be lowered. Meanwhile, there is a possibility that a load for APC becomes larger as the interval of timings becomes shorter. For example, the sample timing may be set as appropriate on the basis of such a viewpoint and the like.

Heretofore, in the light source apparatus 40 of this embodiment, the laser light sources 44 are driven by the delay modulation signal D obtained by delaying the received pulse modulation signal M. Then, the PD signal P is sampled by the falling timing of the pulse modulation signal M. Accordingly, it becomes possible to perform appropriate sampling irrespective of where the pulse modulation signal M has been output from.

As a result, even in a case where the pulse modulation signal M is output from the external apparatus 90 or the system controller 31, sampling can be executed at appropriate timings without raising the load of the light source control unit 42. For example, in a case of driving the laser light sources 44 in synchronization with the photographing operation of the image pickup device 14, the external image pickup apparatus, or the like, APC can be executed with high accuracy without raising the load of the light source control unit 42. Moreover, even in a case where the pulse modulation signal M is output by the light source control unit 42, sampling can be performed by outputting the pulse modulation signal M to the light amount detection unit 43, so the load of the light source control unit 42 can be suppressed.

Further, a signal waveform or the like of the pulse modulation signal M generated by the external apparatus 90 or the like may be slightly changed before being input to the light source unit 41. In the present technology, an appropriate sample timing can be generated in accordance with the waveform of the received pulse modulation signal M. Therefore, even if the waveform is slightly deformed before being input to the light amount detection unit 43, an appropriate sample timing corresponding to the deformation can be generated.

Regarding the PD signal P shown in FIG. 3, the rising edge portion is influenced by a response velocity of the laser light sources 44 and the like and becomes unstable in many cases. Meanwhile, a signal level of the falling edge portion is stable. Since it is possible to sample the PD signal P having a stable falling portion in the present technology, highly-accurate APC can be executed on the basis of the sampled signal R.

Like the endoscope apparatus 100 described in this embodiment, in the medical field or the like, it is extremely important to illuminate the to-be-observed area while maintaining a certain light amount. In this embodiment, it is possible to highly accurately control the output of the laser light sources 44 on the basis of appropriate sampling, and this is extremely effective in performing observation, examination, treatment, and the like.

It should be noted that the present technology is applicable to not only the endoscope apparatus but also other apparatuses and systems in medical and biological fields, such as a light microscope. In addition, the light source apparatus and light source driving method (sampling method) according to the present technology may also be applied to apparatuses and systems of various fields, such as an optical recording system and a semiconductor exposure apparatus.

Other Embodiments

The present technology is not limited to the embodiment described above, and various other embodiments can be realized.

Figure 4:
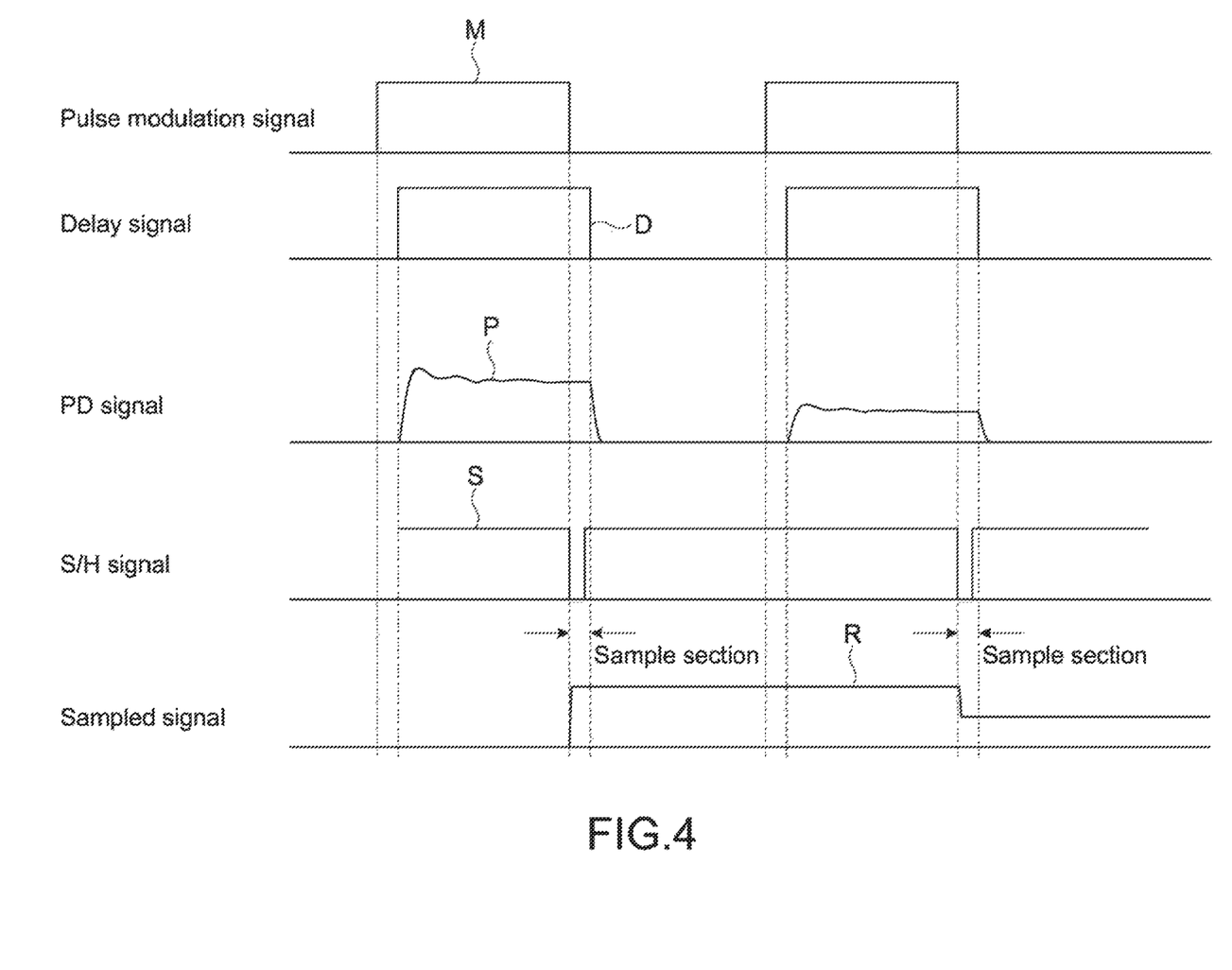
FIG. 4 A timing chart diagram showing another sampling operation example.

FIG. 4 is a timing chart diagram showing another sampling operation example. As shown in FIG. 4, a signal that becomes a LO level at a sample timing may be output as the S/H signal S. An adequate S/H signal only needs to be generated in accordance with sampling characteristics of an S/H circuit, that is, which of rise and fall of an S/H signal the sampling is to be executed at.

A plurality of light amount detection units 43 may be provided in accordance with the number of laser light sources 44. Alternatively, a plurality of predetermined blocks may be provided in the light amount detection unit 43 in accordance with the number of laser light sources 44. Of course, the light amount of each of the plurality of laser light sources 44 may be sampled by the single light amount detection unit 43.

Without being limited to the PWM control and illumination switch, the present technology is also applicable to a case where pulse modulation signals are output for, for example, PNM (Pulse Number Modulation) control, PAM (Pulse Amplitude Modulation) control, PDM (Pulse Density Modulation) control, and the like.

The light amount detection unit 43 shown in FIGS. 1 and 2 may be configured as a light source driving apparatus according to the present technology. For example, a control block that controls the respective blocks shown in FIG. 2 is provided so as to configure the light source driving apparatus according to the present technology as an independent apparatus or unit. In addition, the light source driving apparatus is incorporated into a light source apparatus including a light source, various apparatuses, and the like. The sampling method according to the present technology is executed by the control block of the light source driving apparatus and the control block of the light source apparatus and the like cooperating with each other. Of course, the configuration is not limited to such a configuration.

At least two of the feature portions according to the present technology described above can be combined. In other words, various feature portions described in the respective embodiments may be arbitrarily combined without distinguishing the embodiments from one another. Moreover, the various effects described above are mere examples and should not be limited thereto, and other effects may also be exerted.

It should be noted that the present technology can also take the following configurations.

(1) A light source driving apparatus, including:
a reception unit that receives a pulse modulation signal for pulse-driving a light source;
an output unit that outputs a delay modulation signal obtained by delaying the received pulse modulation signal to the light source;
a sample unit that samples, at a predetermined timing, a light amount of the light source driven on the basis of the delay modulation signal; and
a timing output unit that outputs, to the sample unit, a pulse fall timing of the received pulse modulation signal as the predetermined timing.

(2) The light source driving apparatus according to (1), in which
the reception unit receives a stationary signal for stationarily driving the light source,
the light source driving apparatus further includes a judgment unit that judges which of the pulse modulation signal and the stationary signal a signal received by the reception unit is, and
the timing output unit outputs, in a case where a result of the judgment by the judgment unit is the stationary signal, a stationary drive timing for sampling a light amount of the light source to be stationarily driven.

(3) The light source driving apparatus according to (2), in which
the stationary drive timing is a preset fixed timing.

(4) The light source driving apparatus according to (2) or (3), in which
the reception unit is capable of receiving the pulse modulation signal or the stationary signal output from an external apparatus.

(5) The light source driving apparatus according to any one of (1) to (4), in which
the sample unit stores a sampling result after an elapse of a predetermined response time since the predetermined timing, and
the output unit causes the pulse modulation signal to be delayed by a time longer than the predetermined response time.

REFERENCE SIGNS LIST

D delay modulation signal
M pulse modulation signal
P PD signal

S S/H signal
R sampled signal
40 light source apparatus
42 light source control unit
43 light amount detection unit
44 laser light source
51 multiplication circuit
52 delay circuit
53 signal judgment circuit
54 PWM trigger generation circuit
55 stationary signal trigger generation circuit
56 output switch
57 S/H circuit
58 AD conversion unit
59 sensor unit
90 external apparatus
100 endoscope apparatus

The invention claimed is:

1. A light source driving apparatus, comprising:
a reception unit that receives a pulse modulation signal for pulse-driving a light source;
an output unit that outputs a delay modulation signal obtained by delaying the received pulse modulation signal to the light source;
a sample unit that samples, at a predetermined timing, a light amount of the light source driven on the basis of the delay modulation signal; and
a timing output unit that outputs, to the sample unit, a pulse fall timing of the received pulse modulation signal as the predetermined timing.

2. The light source driving apparatus according to claim 1, wherein
the reception unit receives a stationary signal for stationarily driving the light source,
the light source driving apparatus further comprises a judgment unit that judges which of the pulse modulation signal and the stationary signal a signal received by the reception unit is, and
the timing output unit outputs, in a case where a result of the judgment by the judgment unit is the stationary signal, a stationary drive timing for sampling a light amount of the light source to be stationarily driven.

3. The light source driving apparatus according to claim 2, wherein
the stationary drive timing is a preset fixed timing.

4. The light source driving apparatus according to claim 2, wherein
the reception unit is capable of receiving the pulse modulation signal or the stationary signal output from an external apparatus.

5. The light source driving apparatus according to claim 1, wherein
the sample unit stores a sampling result after an elapse of a predetermined response time since the predetermined timing, and
the output unit causes the pulse modulation signal to be delayed by a time longer than the predetermined response time.

6. The light source driving apparatus according to claim 1,
wherein the light source driving apparatus is applicable to a medical imaging apparatus, and
wherein the medical imaging apparatus is one of an endoscope apparatus or a microscope apparatus.

7. A light source driving method, comprising:
outputting a delay modulation signal obtained by delaying a pulse modulation signal for pulse-driving a light source, to the light source; and
sampling a light amount of the light source driven on the basis of the delay modulation signal at a pulse fall timing of the pulse modulation signal.

8. A light source driving system, comprising:
a light source;
a reception unit that receives a pulse modulation signal for pulse-driving the light source;
an output unit that outputs a delay modulation signal obtained by delaying the received pulse modulation signal to the light source;
a sample unit that samples, at a predetermined timing, a light amount of the light source driven on the basis of the delay modulation signal;
a timing output unit that outputs, to the sample unit, a pulse fall timing of the received pulse modulation signal as the predetermined timing; and
a control unit that controls an output of the light source on the basis of a result of the sampling by the sample unit.

* * * * *